(12) United States Patent
Shields et al.

(10) Patent No.: US 7,682,399 B2
(45) Date of Patent: Mar. 23, 2010

(54) ACETABULAR SHELL

(75) Inventors: William Hale Shields, Union City, NJ (US); Viktor Erik Krebs, Rocky River, OH (US)

(73) Assignee: Howmedica Osteonics Corp., Mahwah, NJ (US)

( * ) Notice: Subject to any disclaimer, the term of this patent is extended or adjusted under 35 U.S.C. 154(b) by 151 days.

(21) Appl. No.: 11/810,829

(22) Filed: Jun. 6, 2007

(65) Prior Publication Data

US 2008/0306606 A1 Dec. 11, 2008

(51) Int. Cl.
*A61F 2/34* (2006.01)
(52) U.S. Cl. .............. 623/22.24; 623/22.21; 623/22.28; 623/22.35; 623/22.32; 623/22.38
(58) Field of Classification Search .............. 623/22.11, 623/22, 12, 22.14–22.19, 22.21, 22.24–22.26, 623/22.28, 22.32, 22.34–22.38
See application file for complete search history.

(56) References Cited

U.S. PATENT DOCUMENTS

| 2,947,308 | A | 8/1960 | Gorman |
| 4,919,675 | A | 4/1990 | Dietschi et al. |
| 5,314,490 | A | 5/1994 | Wagner et al. |
| 5,425,778 | A | 6/1995 | Zichner et al. |
| 5,702,477 | A | 12/1997 | Capello et al. |
| 5,871,548 | A | 2/1999 | Sanders et al. |
| 5,879,399 | A * | 3/1999 | Church .................... 623/22.25 |
| 5,931,870 | A | 8/1999 | Cuckler et al. |
| 6,340,370 | B1 | 1/2002 | Willert et al. |
| 6,416,553 | B1 | 7/2002 | White et al. |
| 6,454,809 | B1 | 9/2002 | Tornier et al. |
| 6,458,161 | B1 | 10/2002 | Gibbs et al. |
| 6,908,486 | B2 | 6/2005 | Lewallen |
| 2003/0153982 | A1 | 8/2003 | Pria |
| 2003/0212459 | A1 | 11/2003 | Gibbs |
| 2004/0199258 | A1* | 10/2004 | Macara .................... 623/22.32 |
| 2005/0021148 | A1 | 1/2005 | Gibbs |
| 2005/0288793 | A1* | 12/2005 | Dong et al. .............. 623/22.28 |
| 2006/0190089 | A1 | 8/2006 | Montoya et al. |

* cited by examiner

*Primary Examiner*—Corrine M McDermott
*Assistant Examiner*—Rebecca Straszheim
(74) *Attorney, Agent, or Firm*—Lerner, David, Littenberg, Krumholz & Mentlik, LLP

(57) ABSTRACT

An acetabular cup assembly for a prosthetic hip joint is disclosed. This assembly includes an outer shell having at least one shell extension, an adaptor having at least one adaptor extension, and an insert. The inclusion of an extension on the outer shell and an extension on the adaptor allows for easier manipulation and implantation of the assembly.

16 Claims, 18 Drawing Sheets

ACETABULAR SHELL

BACKGROUND OF THE INVENTION

The present invention relates generally to orthopedics and, in particular, to an acetabular prosthetic implant.

Total hip replacement surgery typically entails the removal and replacement of the femoral head portion of the femur, as well as the resurfacing and replacement of the acetabulum. In both cases, prosthetic implants are utilized to replace the removed bone portions. Although these types of surgeries have become rather common place, surgeons are often faced with decisions during surgery relating to the particular prosthetic implants utilized, in addition to their respective orientation and positioning. For example, acetabular cup replacements may require a surgeon to first implant a shell portion and thereafter select different cup inserts and position them with respect to the shell portion. Several attempts at providing beneficial acetabular cup assemblies have been developed heretofore. Some examples of such acetabular cup assembly designs are disclosed in U.S. Pat. No. 6,475,243 ("the '243 patent") and U.S. Pat. No. 6,610,097 ("the '097 patent"), and U.S. Patent Application Publication Nos. 2005/0288793 ("the '793 application") and 2006/0190089 ("the '089 application"), the disclosures of which are hereby incorporated by reference herein.

The variety of conditions encountered when utilizing such implants has led to the use of various bearing materials and attachment methods placed at an optimum position and orientation, as determined by conditions encountered at the site of the implant. The choice of particular material for the bearing, as well as the size, positioning and orientation of the bearing member, is determined by the surgeon performing the procedure. Usually such choices are made on the basis of a pre-operative assessment of the needs of a particular patient. However, some times the choices are not apparent until the implant site is actually being prepared and the conditions encountered at the site can be evaluated during the implantation procedure itself. Accordingly, it would be advantageous to have available a greater range of interoperative choices, as well as pre-operative choices, so as to enable a surgeon to accommodate the needs of a particular patient as determined by either or both a pre-operative assessment and an evaluation of conditions encountered at a particular implant site, and to do so in a practical manner.

Especially in the case of revision surgical procedures wherein the pelvis has been severely compromised or deteriorated, it is known to use support structures to receive an acetabular prosthetic device. For example, in the '793 application, the invention disclosed relates to optional modular adaptors which include wings, straps, or flanges to enhance the support of the acetabular prosthesis on the pelvis. Often times, devices including such extensions for connection with the pelvis, while often necessary, are difficult to insert through an incision and manipulate at the implantation site. Specifically, devices having multiple extensions extending in opposition or different directions often require a significant amount of unneeded or unwanted added manipulation on the part of a surgeon.

Therefore, there exists a need for an easily implantable acetabular prosthetic device including supports or extensions for connection with the pelvis or other surrounding bone.

SUMMARY OF THE INVENTION

A first aspect of the present invention is an acetabular cup assembly for a prosthetic hip joint. In accordance with one embodiment of the present invention, the assembly includes an outer shell for attachment to the acetabulum, with the outer shell having an inner surface and at least one radially extending shell extension, a bearing insert, and an adaptor having an outer surface for engaging the inner surface of the outer shell, an inner surface for receiving the bearing insert portion, and at least one radially extending adaptor extension.

In accordance with certain other embodiments of the present invention, the at least one shell extension and at least one adaptor extension may each include at least one aperture, and such may also include a plurality of apertures. In other embodiments, at least one of the at least one shell extension and at least one adaptor extension are deformable at least in one direction, and a reduced cross-section may facilitate the deformation. The reduced cross-section may be formed by a groove. Both the at least one shell extension and the at least one adaptor extension are deformable. Preferably, the inner surface of the outer shell and the outer surface of the adaptor have complimentary tapered locking surfaces, and the adaptor may include a plurality of anti-rotation scallops for cooperation with complimentary structure on the outer shell. In other preferred embodiments, the at least one shell extension is shaped to cooperate with an illium, and the at least one adaptor extension is shaped to cooperate with an ischium. Finally, in certain embodiments, the adaptor includes a rim area, with the at least one adaptor extension extending from the rim area.

A second aspect of the present invention is a kit for resurfacing an acetabulum. In accordance with one embodiment of this second aspect, the kit includes at least one outer shell for attachment to the acetabulum, with the outer shell having an inner surface and at least one radially extending shell extension, at least one bearing insert, and a plurality of adaptors each having an outer surface for engaging the inner surface of the outer shell, an inner surface for receiving the bearing insert portion, and at least one radially extending adaptor extension.

In certain kit embodiments, the inner surface of the outer shell and the outer surfaces of the plurality of adaptors may have complimentary tapered locking surfaces, and the plurality of adaptors may each include a plurality of anti-rotation scallops for cooperation with a complimentary structure on the outer shell. The inner surfaces of the plurality of adaptors and an outer surface of the at least one bearing insert may have complimentary locking surfaces. In other embodiments, the at least one adaptor extension varies for each adaptor in the kit.

A third aspect of the present invention is a method of implanting an acetabular portion of a prosthetic hip joint. In accordance with one embodiment of this third aspect of the present invention, the method includes the step of preparing an acetabulum of a patient, providing an outer shell for attachment to the acetabulum, with the outer shell having at least one radially extending shell extension, providing a bearing insert, providing an adaptor having at least one radially extending adaptor extension, inserting the outer shell into the prepared acetabulum, connecting the at least one shell extension to the patient, inserting the adaptor into the outer shell, connecting the at least one adaptor extension to the patient, and inserting the bearing insert into the adaptor.

In certain embodiments of this third aspect method, the shell extension connecting step includes connecting the at least one shell extension to an illium of the patient. In other or the same embodiments, the adaptor extension connecting step includes connecting the at least one adaptor extension to an ischium of the patient.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

As used herein, when referring to bones or other parts of the body, the term "proximal" means closer to the heart and the term "distal" means more distant from the heart. The term "inferior" means lower or bottom and the term "superior" means upper or top. The term "anterior" means towards the front part of the body or the face and the term "posterior" means towards the back of the body. The term "medial" means toward the midline of the body and the term "lateral" means away from the midline of the body.

Figure 1:
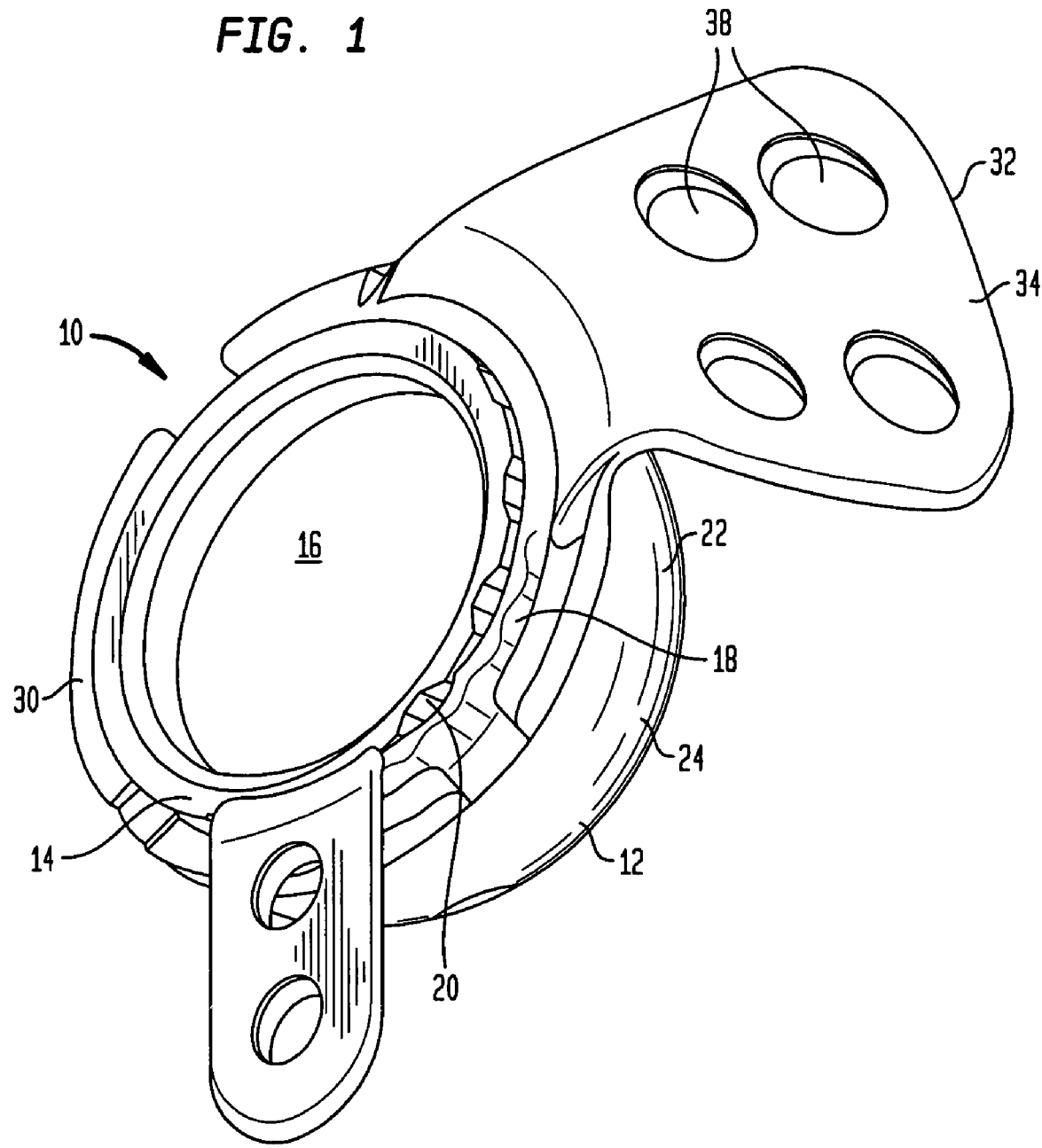
FIG. 1 is perspective view of an acetabular cup replacement assembly according to a first embodiment of the present invention.
Figure 2:
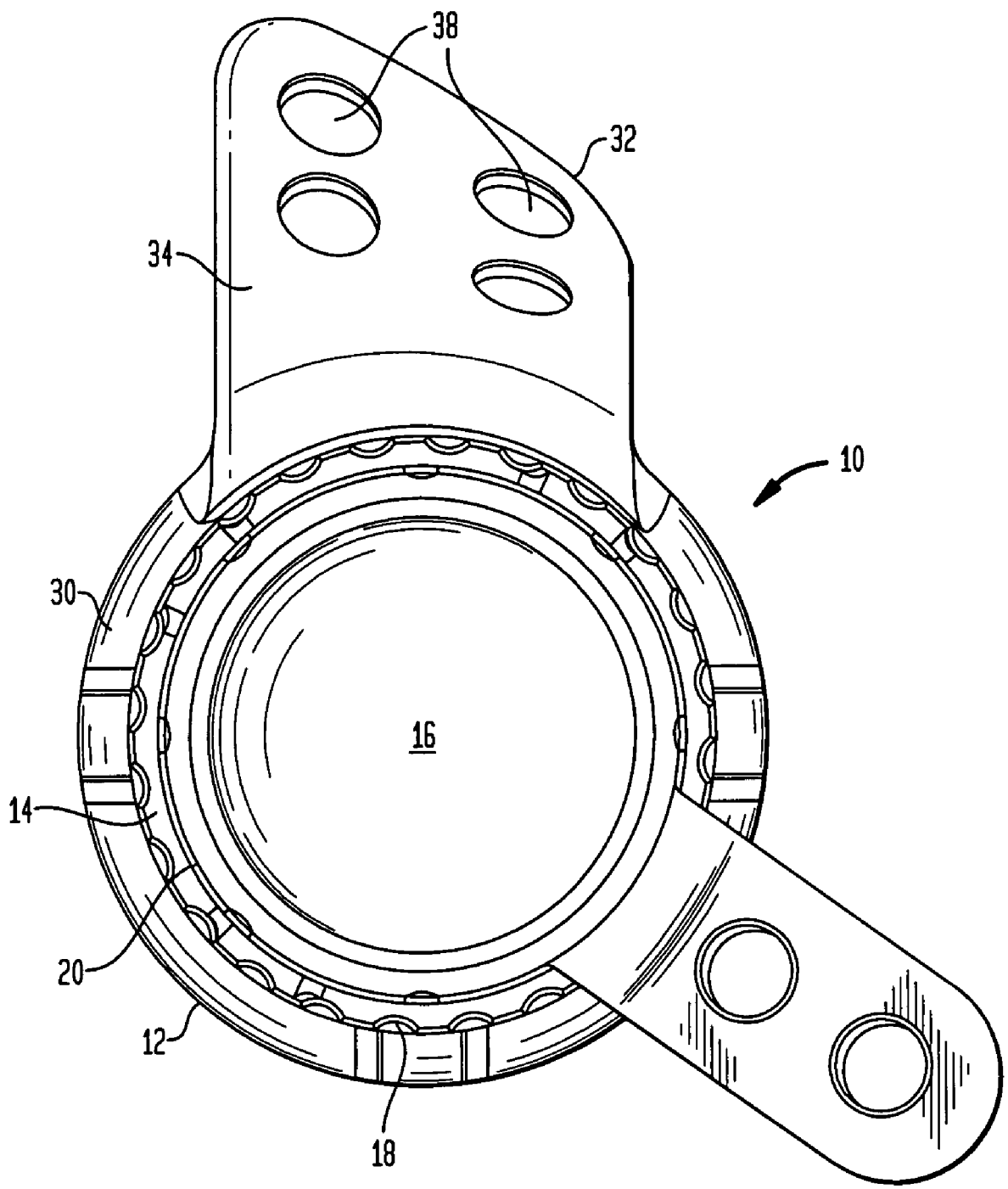
FIG. 2 is a top view of the acetabular cup replacement assembly of FIG. 1.
Figure 3:
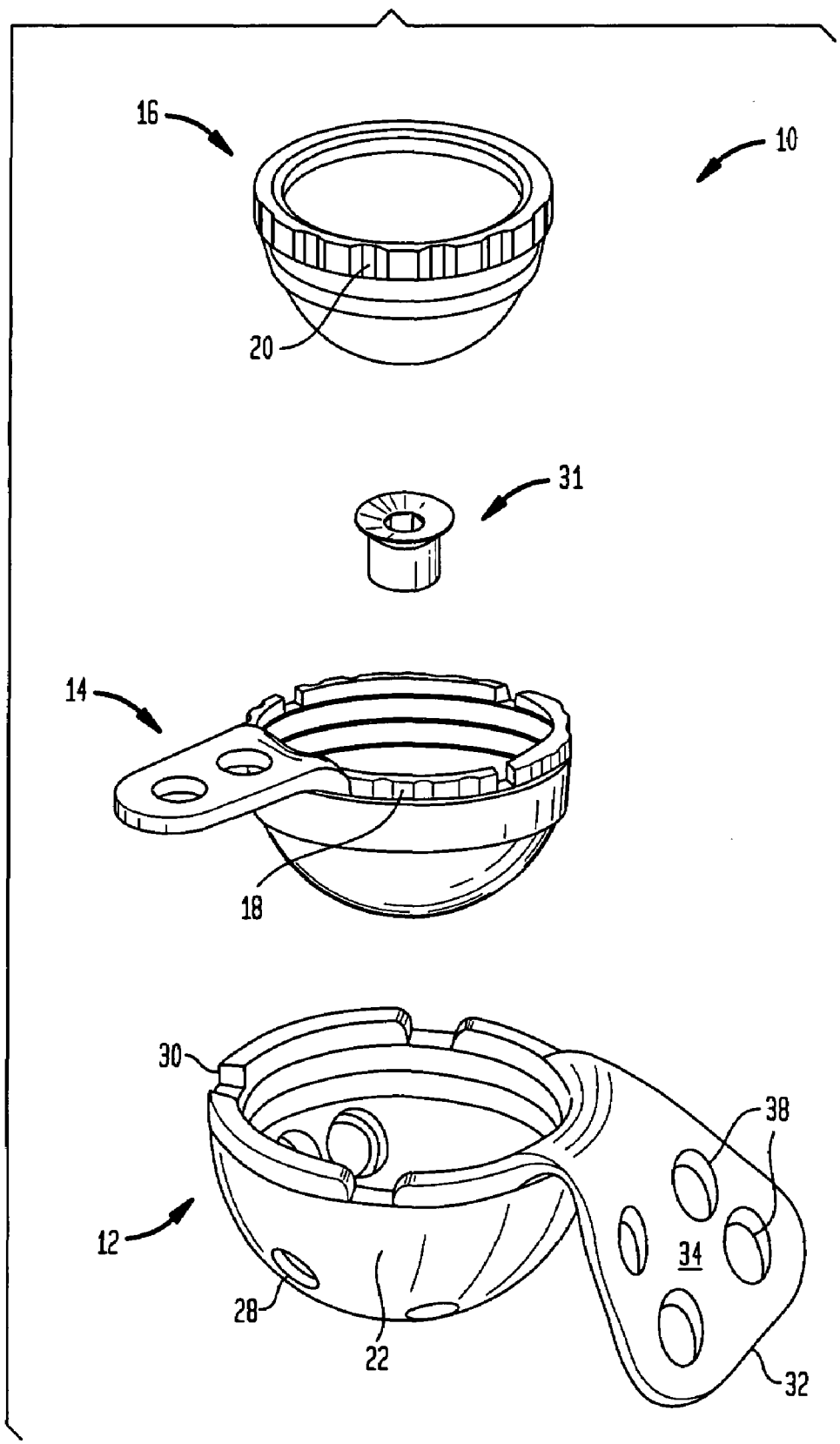
FIG. 3 is an exploded view of the acetabular cup replacement assembly of FIG. 1.

Referring to the drawings, wherein like reference numerals refer to like elements, there is shown in FIGS. 1-3, an acetabular cup replacement assembly designated generally by reference numeral 10. As shown in those figures, assembly 10 includes an outer shell portion 12, an adaptor portion 14, and an insert portion 16. Adaptor 14 is preferably designed both to be received within outer shell 12 and to receive insert 16. However, it is noted that shell 12 may also be capable of receiving insert 16 directly. Of course, this would require the use of a larger insert 16 than one which is to be received in adaptor 14. Preferably, an insert 16 to be received directly into outer shell 12 would exhibit size and shape parameters similar to that of adaptor 14 designed to likewise be received in shell 12. In all cases, shell 12 is preferably sized and shaped to be received within an already prepared acetabulum of a patient, and all other components of assembly 10 are to be sized and shaped according to the selected shell 12. It is to be understood that preparation of the acetabulum of a patient is preferably done in accordance with well known and well developed surgical procedures often employed during a total hip replacement. Those of ordinary skill in the art would recognize such and also any procedures created subsequent to the present invention that could likewise be utilized.

The specific interconnection among the various components of assembly 10 will not be discussed in detail herein. Rather, it is to be understood that the interconnection among shell 12, adaptor 14, and insert 16 results from previously developed and/or used devices, such as taper connections among the various elements. For example, the '243 patent, the '097 patent, the '793 application, and the '089 application, which are all incorporated by reference herein in their entirety, teach various interconnections that may be employed by the present invention. It is to be understood that this list of incorporated references is by no means exhaustive, and also includes U.S. Patent Application Publication No. 2007/0106392 ("the '392 application") filed on Nov. 8, 2005, the disclosure of which is also hereby incorporated by reference herein, among others. In the embodiment depicted in FIGS. 1-9, adaptor 14 includes anti-rotation scallops 18 for cooperation with complimentary structure on shell 12 and insert 16 includes anti-rotation scallops 20 for cooperation with complimentary structure on adaptor 14. Scallops 18 prevent rotation of adaptor 14 with respect to shell 12, and scallops 20 prevent rotation of insert 16 with respect to adaptor 14. However, it is noted that other structure may be employed, as set forth in the incorporated references or otherwise, and it is also to be understood that such anti-rotation elements are not required in the present invention.

Figure 4:
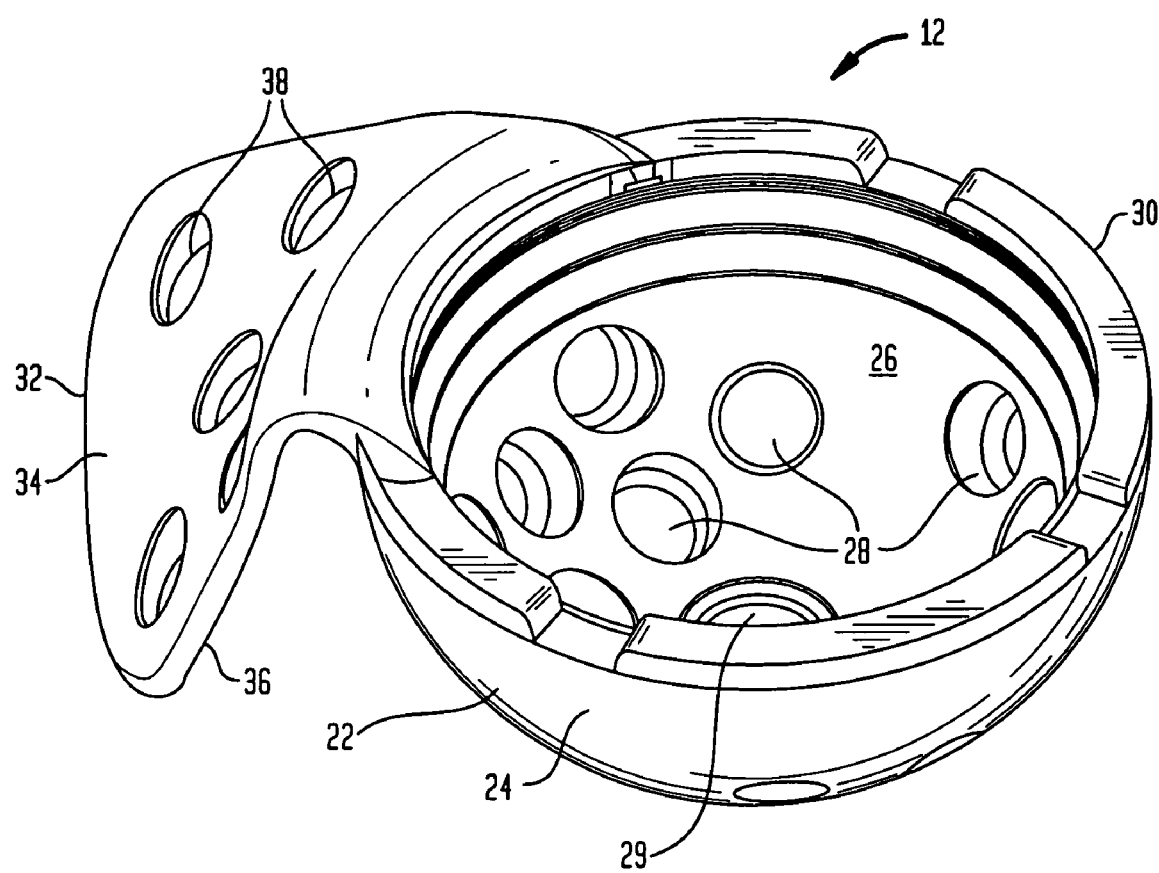
FIG. 4 is a perspective view of an outer shell portion of the acetabular cup replacement assembly of FIG. 1.
Figure 5:
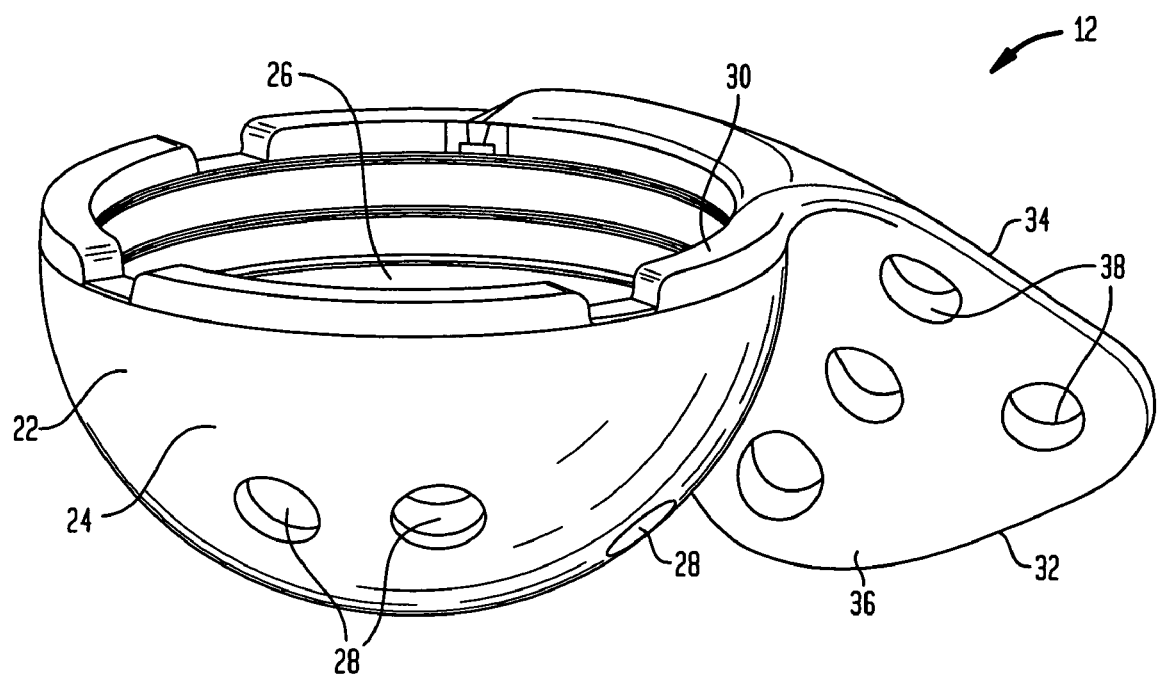
FIG. 5 is another perspective view of the outer shell portion of the acetabular cup replacement assembly of FIG. 1.
Figure 6:
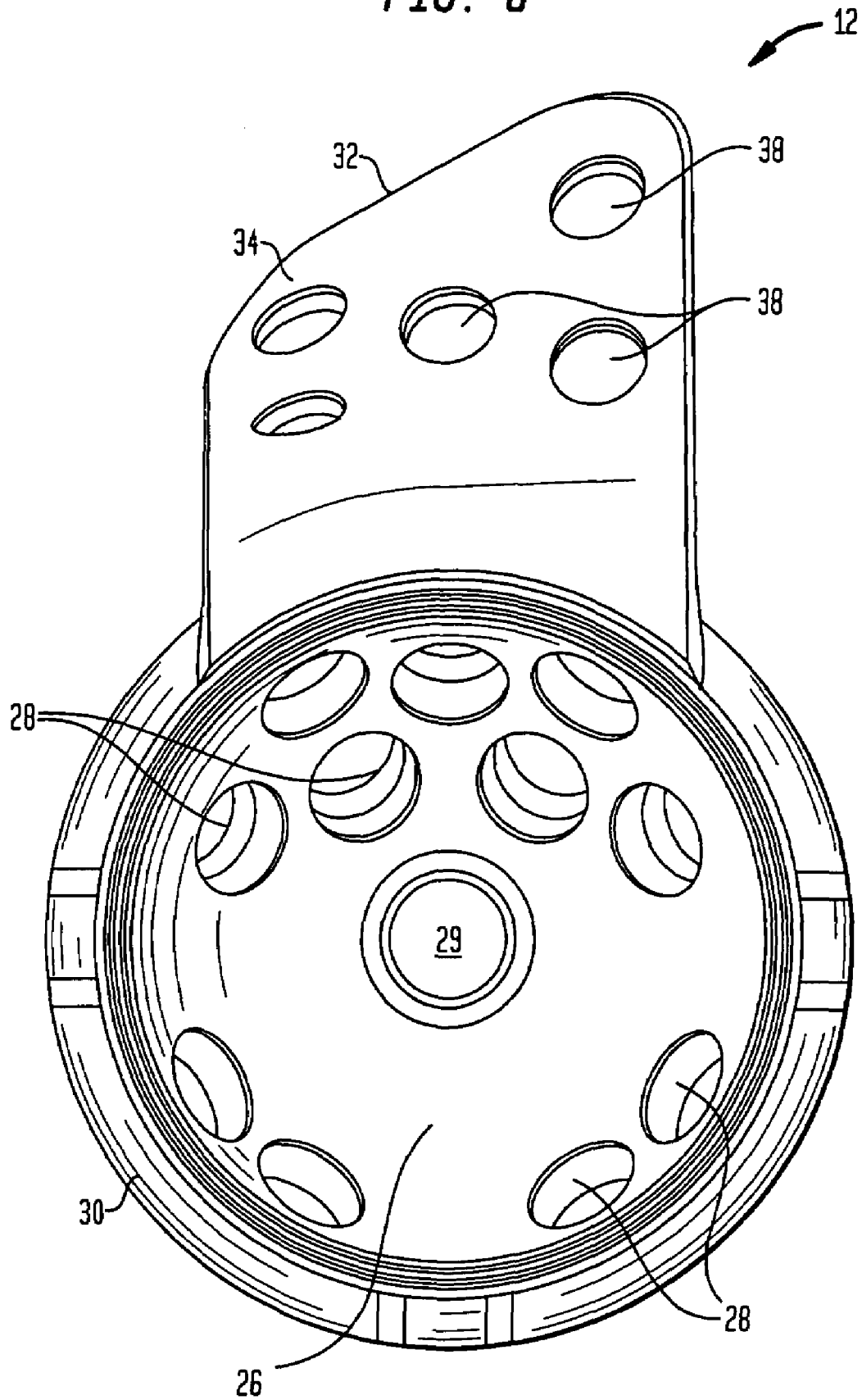
FIG. 6 is a top view of the outer shell portion of the acetabular cup replacement assembly of FIG. 1.

As is best shown in FIGS. 4-6, outer shell 12 includes, among other elements, a semi-circular shell body 22 having an exterior surface 24 and an interior surface 26. Preferably, exterior surface 24 is designed so as to be abutted against an already prepared acetabulum of a patient, while interior surface 26 is designed so as to receive either an appropriately sized adaptor 14 or an appropriately sized insert 16. Shell body 22 may further include one or more shell body apertures 28 that extend from interior surface 26 to exterior surface 24 for receiving bone anchoring elements (not shown) such as screws or pins, and a rim 30 extending around the perimeter of interior surface 26. Extending from rim 30 is a shell flange or shell extension 32. Shell extension 32 includes a top surface 34, a bone contacting bottom surface 36, and one or more shell extension apertures 38 that extend from top surface 34 to bottom surface 36. These apertures 38 are preferably designed to receive bone anchoring elements, like that of body apertures 28. Although shown extending from rim 30, it is to be understood that shell extension 32 could extend from other portions of outer shell 12, including, but not limited to, exterior and interior surfaces 24 and 26. Moreover, although shown as being integral with rim 30, shell extension 32 could be designed to be removably coupled with any portion of outer shell 12.

In the particular design of outer shell 12 best shown in FIGS. 4-6, shell extension 32 is designed so as to cooperate and be anchored to the illium bone of a patient. The particular configuration shown has been created to match traditional patient anatomy and its shape is based on the anatomical study of a plethora of specimens. However, it is to be understood that variously sized and shaped shell extensions 32 may be employed in accordance with the present invention. For instance, shell extension 32 could be configured to cooperate and be anchored to another bone, such as the ischium of a patient. In addition, shell extension 32 may be designed so as to be deformable in at least one direction so as to allow a surgeon the freedom to match patient anatomy in situ. One manner in which this deformable structure may be achieved is more specifically taught in the '793 application, and essentially involves providing shell extension 32 with a reduced cross-section, such as a groove, to facilitate the deformation. In such a case, the surgeon performing the surgery can simply tailor the shape of shell extension 32 to the particular shape, while outer shell is in the body or not. A tool may be necessary to effectuate the deformation. Finally, it is noted that other configurations, some of which are discussed below in relation to an adaptor extension, may similarly be employed with outer shell 12. The particular configuration depends upon the surgeon preference and the particular patient anatomy.

Figure 7:
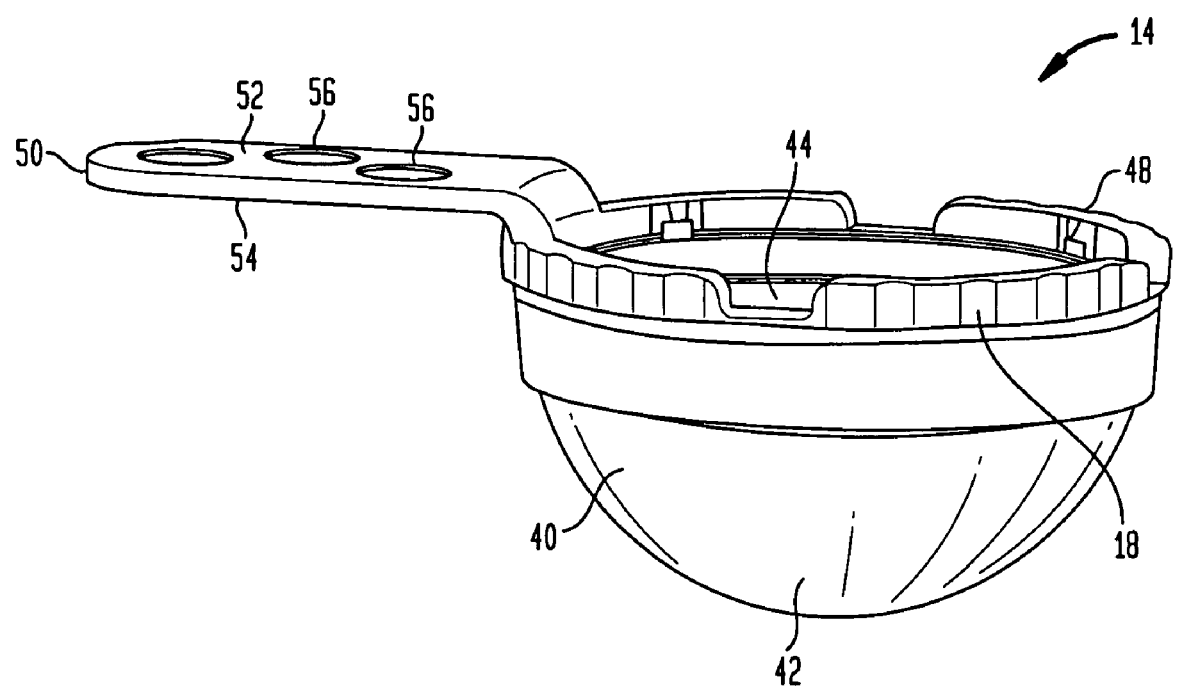
FIG. 7 is a side perspective view of an adaptor portion of the acetabular cup replacement assembly of FIG. 1.
Figure 8:
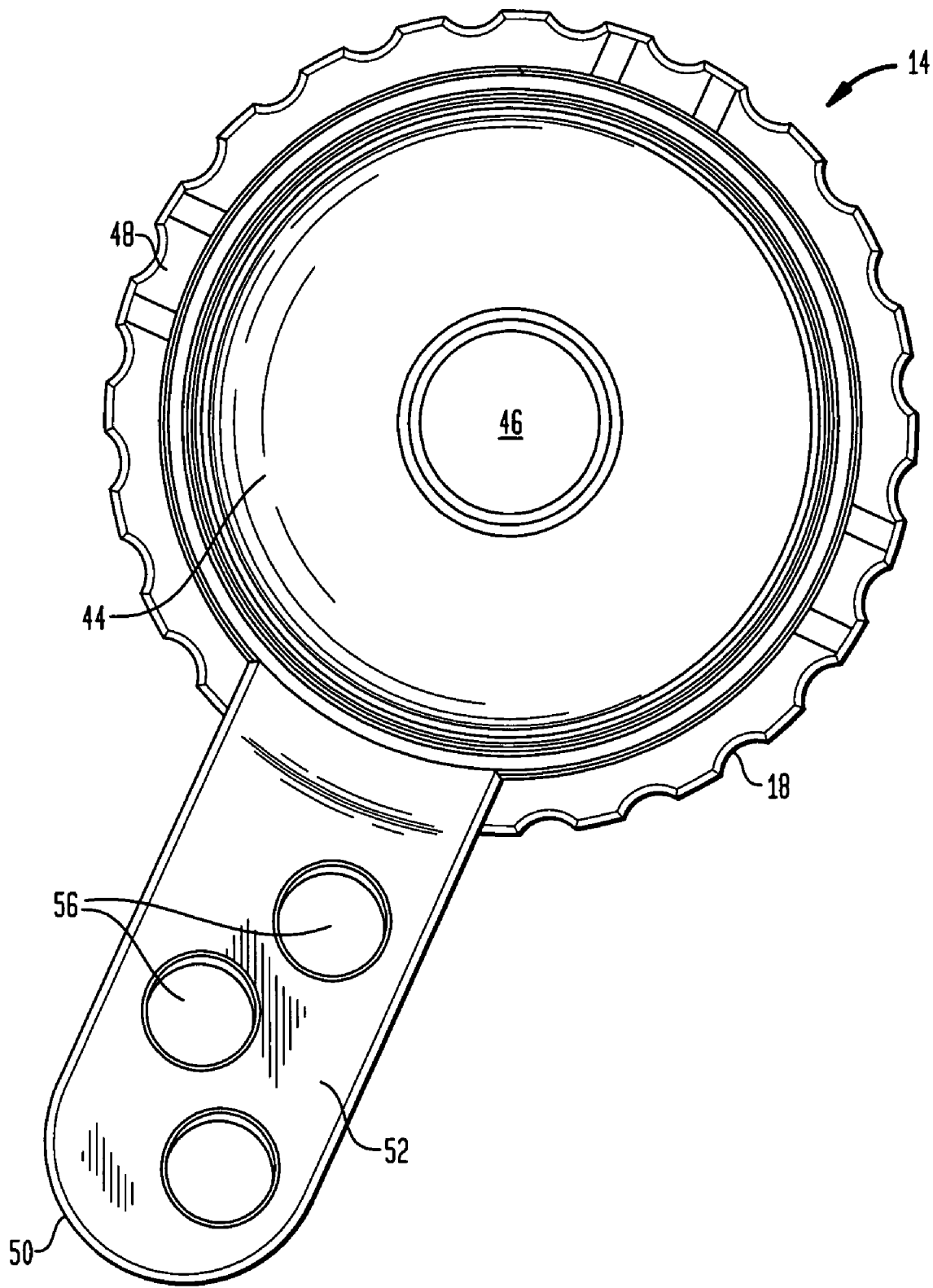
FIG. 8 is a top view of the adaptor portion of the acetabular cup replacement assembly of FIG. 1.

As is best shown in FIGS. 7 and 8, adaptor 14 includes, among other elements, a semi-circular adapter body 40 having an exterior surface 42 and an interior surface 44. Preferably, exterior surface 42 is designed so as to be placed adjacent to or abutted against interior surface 26 of outer shell 12, while interior surface 44 is designed so as to receive an appropriately sized insert 16. It is to be understood that depending upon the specific interconnection employed among the various components, all or only a portion of exterior surface 42 may actually contact interior surface 26. Likewise, depending upon the interconnection configuration, interior surface 44 may contact only a portion or all of insert 16. Unlike body 22 of outer shell 12, body 40 is preferably solid except for one centrally located adaptor body aperture 46 that is preferably designed to align with a similarly centrally located aperture 29 (best shown in FIG. 6) formed in shell body 22. This alignment allows for one relatively short anchoring element 31 (best shown in FIG. 3) to pass through both adaptor 14 and outer shell 12. This preferably adds to the locking of the adaptor to the shell. Adaptor body 40 also preferably includes a rim 48 extending around the perimeter of interior surface 44. The above discussed scallops 18 are situated on rim 48 and extending from rim 48 is an adaptor flange or adaptor extension 50. Adaptor extension 50 includes a top surface 52, a bone contacting bottom surface 54, and one or more adaptor extension apertures 56 that extend from top surface 52 to bottom surface 54. These apertures 56 are preferably designed to receive bone anchoring elements. Although shown extending from rim 48, it is to be understood that adaptor extension 50 could extend from other portions of adaptor 14. Moreover, although shown as being integral with rim 30, shell extension 50 could be designed to be removably coupled with any portion of adaptor 14.

Figure 9:
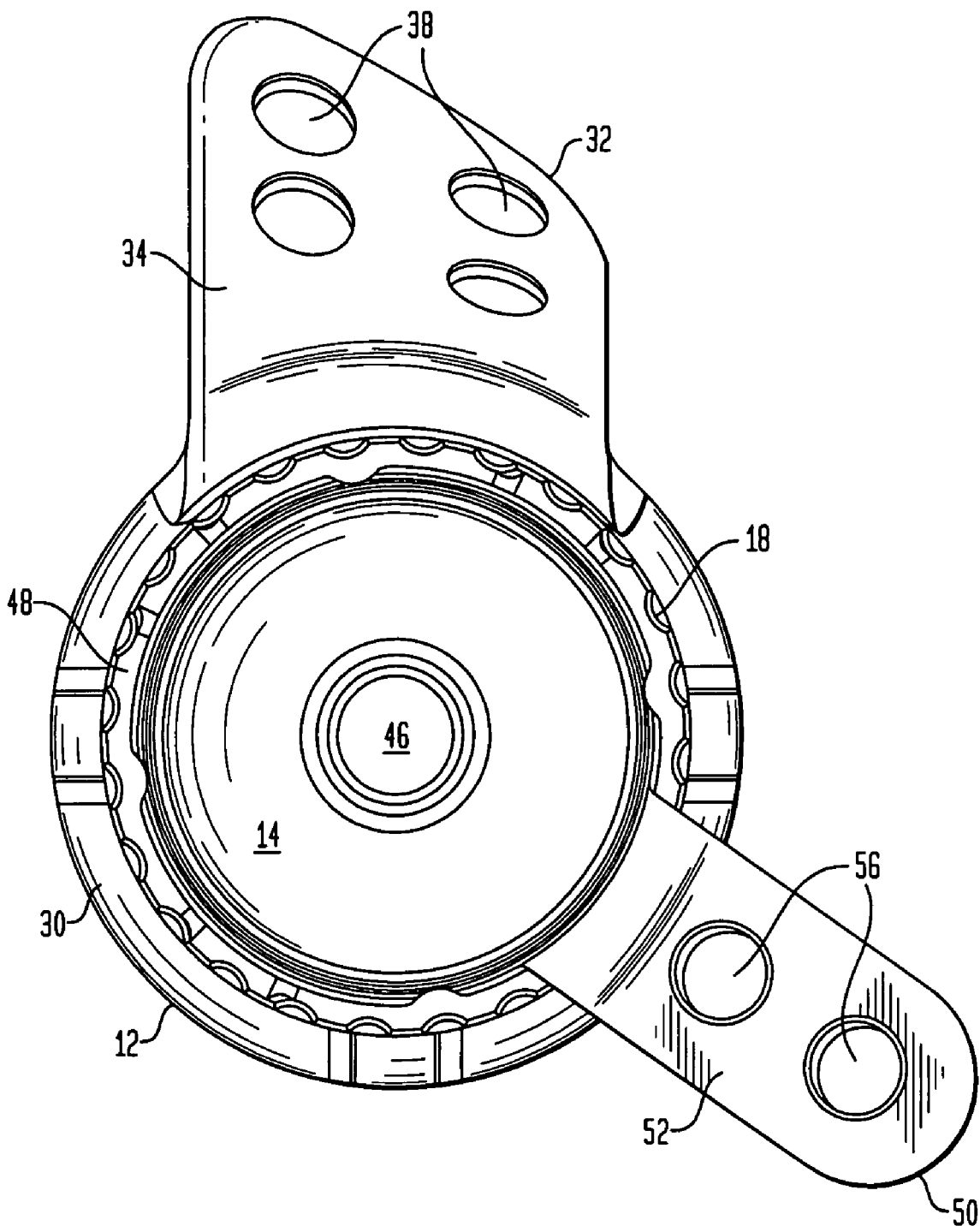
FIG. 9 is a top view depicting the adaptor portion of FIGS. 7 and 8 disposed in the shell portion of FIGS. 4-6.

Like shell extension 32, adaptor extension 50 is configured to cooperate with and be anchored to a bone, in this case, the ischium bone of a patient. Once again, the particular configuration shown has been created to match traditional patient anatomy and its shape is based on the anatomical study of a plethora of specimen, and it is to be understood that variously sized and shaped adaptor extensions 50 may be employed in accordance with the present invention. For instance, adaptor extension 50 could be configured to cooperate and be anchored to another bone, such as the illium of a patient. In addition, adaptor extension 50 may be designed so as to be deformable in at least one direction so as to allow a surgeon the freedom to match patient anatomy in situ, in a similar fashion as is discussed above in relation to shell extension 32. FIG. 9 depicts adaptor 14 disposed within outer shell 12.

Figure 10:
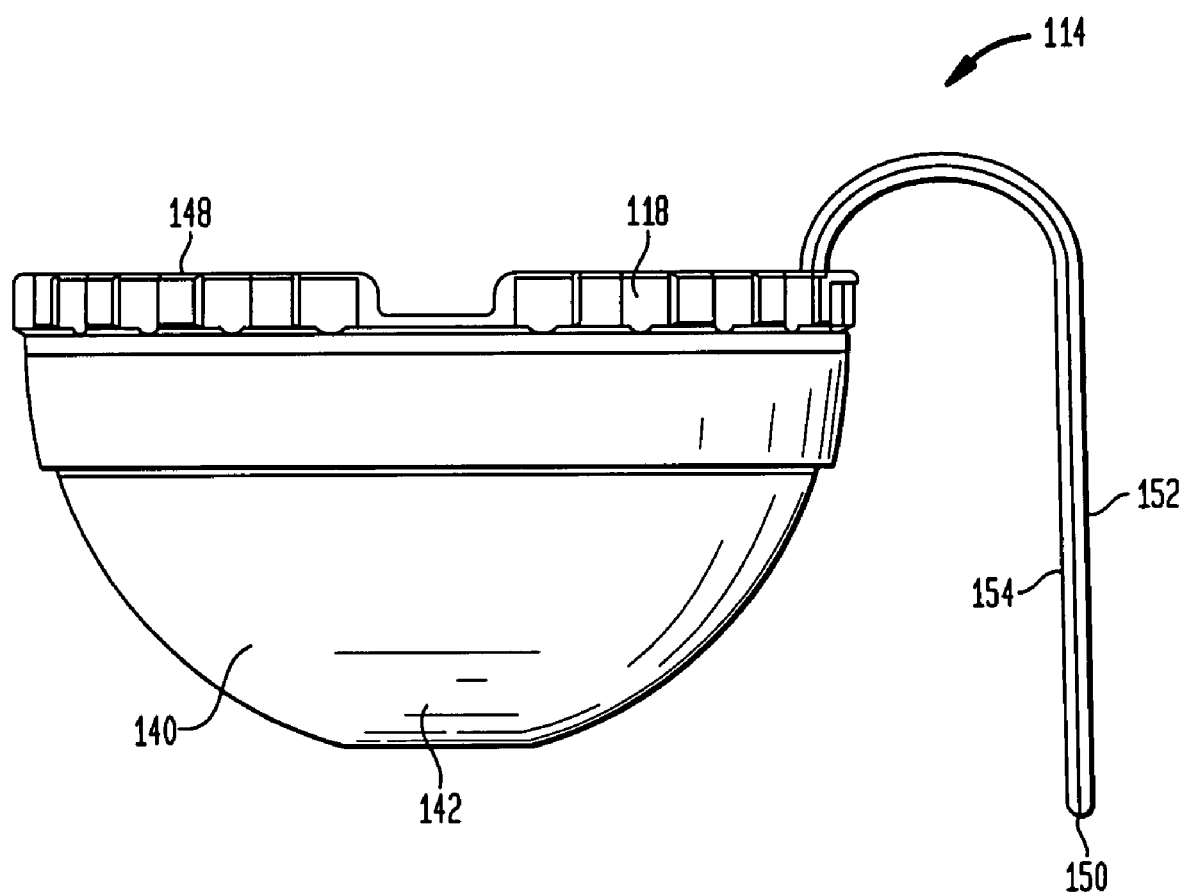
FIG. 10 is a side view of an adaptor portion of an acetabular cup replacement assembly according to another embodiment of the present invention.
Figure 11:
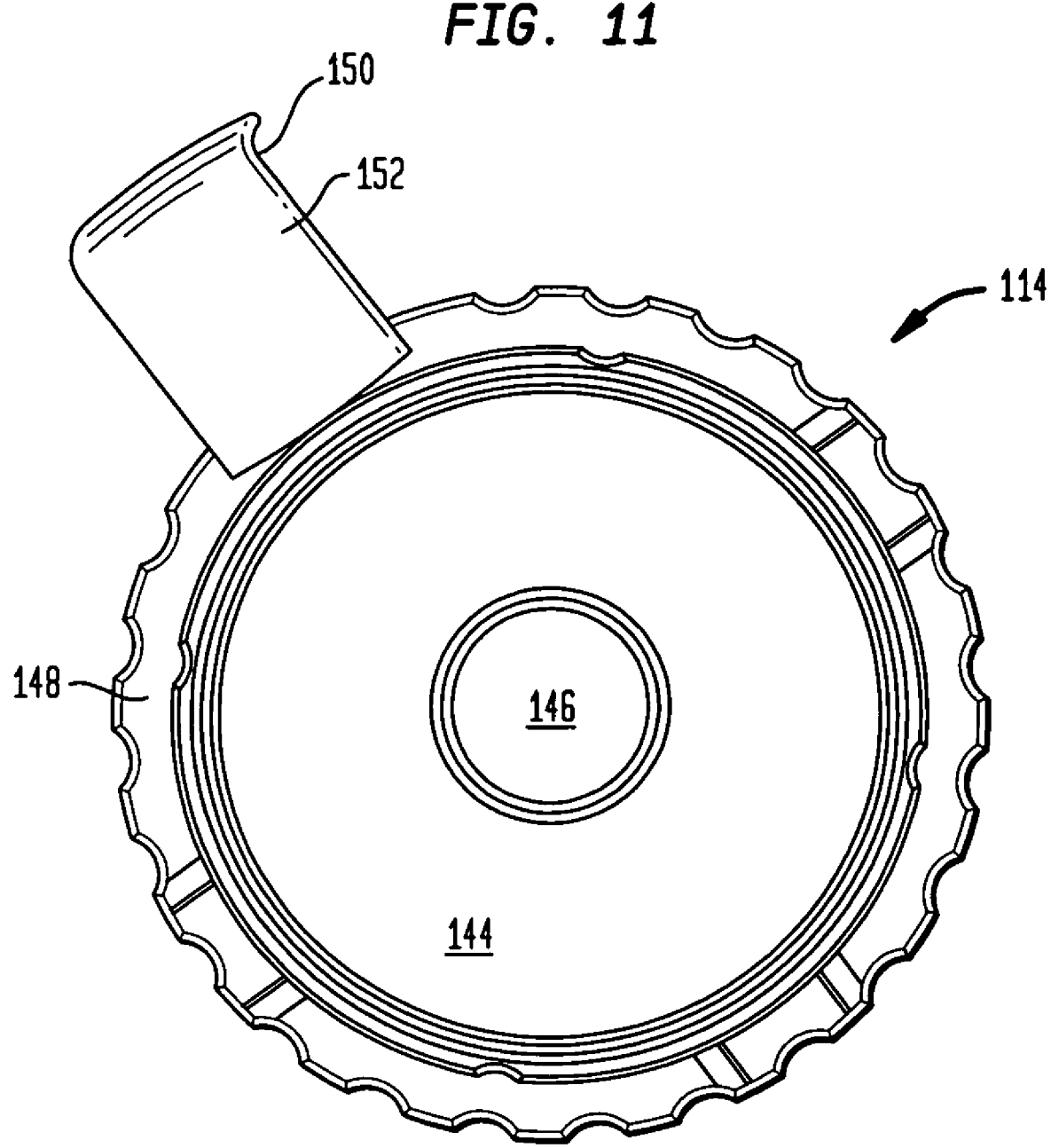
FIG. 11 is a top view of the adaptor portion of FIG. 10.

FIGS. 10-18 depict several different adaptors contemplated in accordance with the present invention. Although not exhaustive, these figures show adaptors which are substantially similar to the above-discussed adaptor 14, except for the inclusion of different flange or extension in each case. The particular embodiment adaptor shown is accorded its own reference number, with similar elements to that of adaptor 14 being accorded similar reference numerals within a larger series of numbers. For example, FIGS. 10 and 11 depict an adaptor 114 including a body 140 having an exterior surface 142, an interior surface 144, a centrally located adaptor body aperture 146, and a rim 148. Adaptor 114 further includes an adaptor extension 150 having a top surface 152 and a bottom surface 154. Although not shown, extension 150 may include one or more apertures for receiving a bone fixation element, similar to that discussed above. Adaptor 114 is substantially similar to that of adaptor 14, except for the fact that extension 150 is of an inferior hook design. Such may useful in certain hip procedures, depending upon anatomical conditions or the preference of a surgeon.

Figure 12:
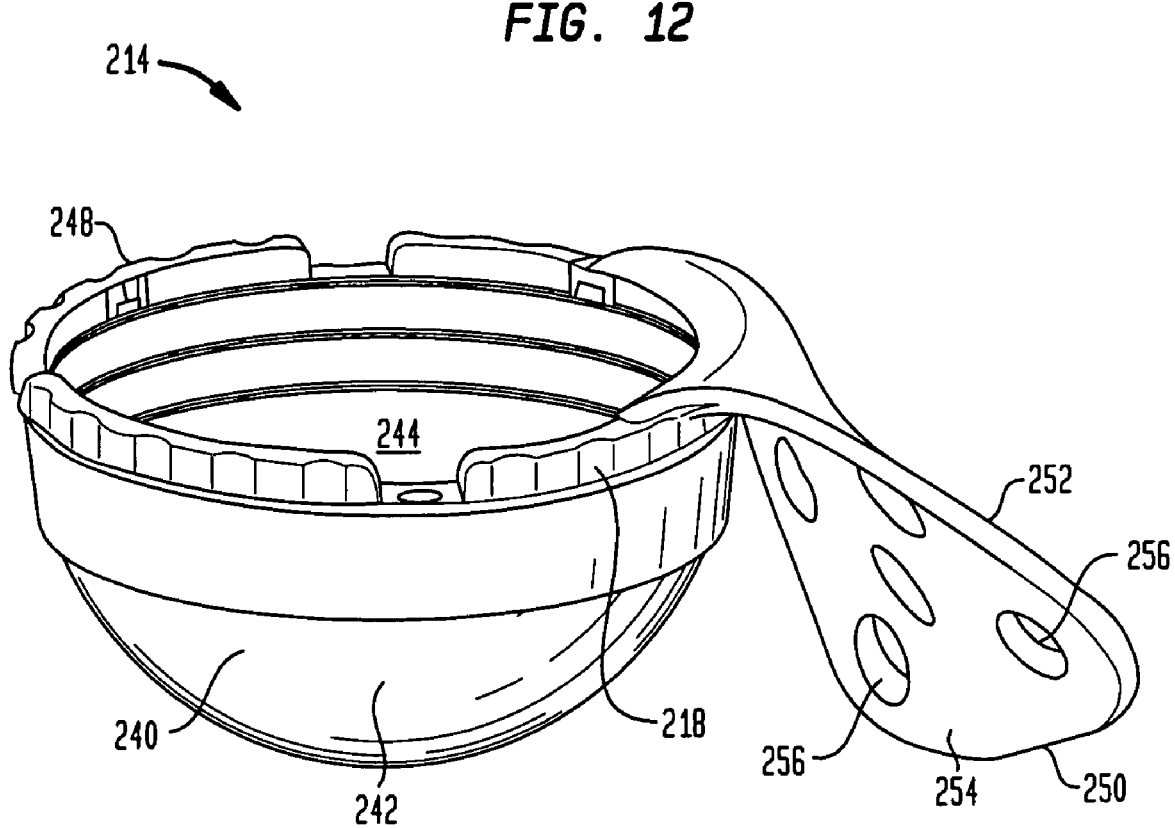
FIG. 12 is a perspective view of an adaptor portion of an acetabular cup replacement assembly according to yet another embodiment of the present invention.
Figure 13:
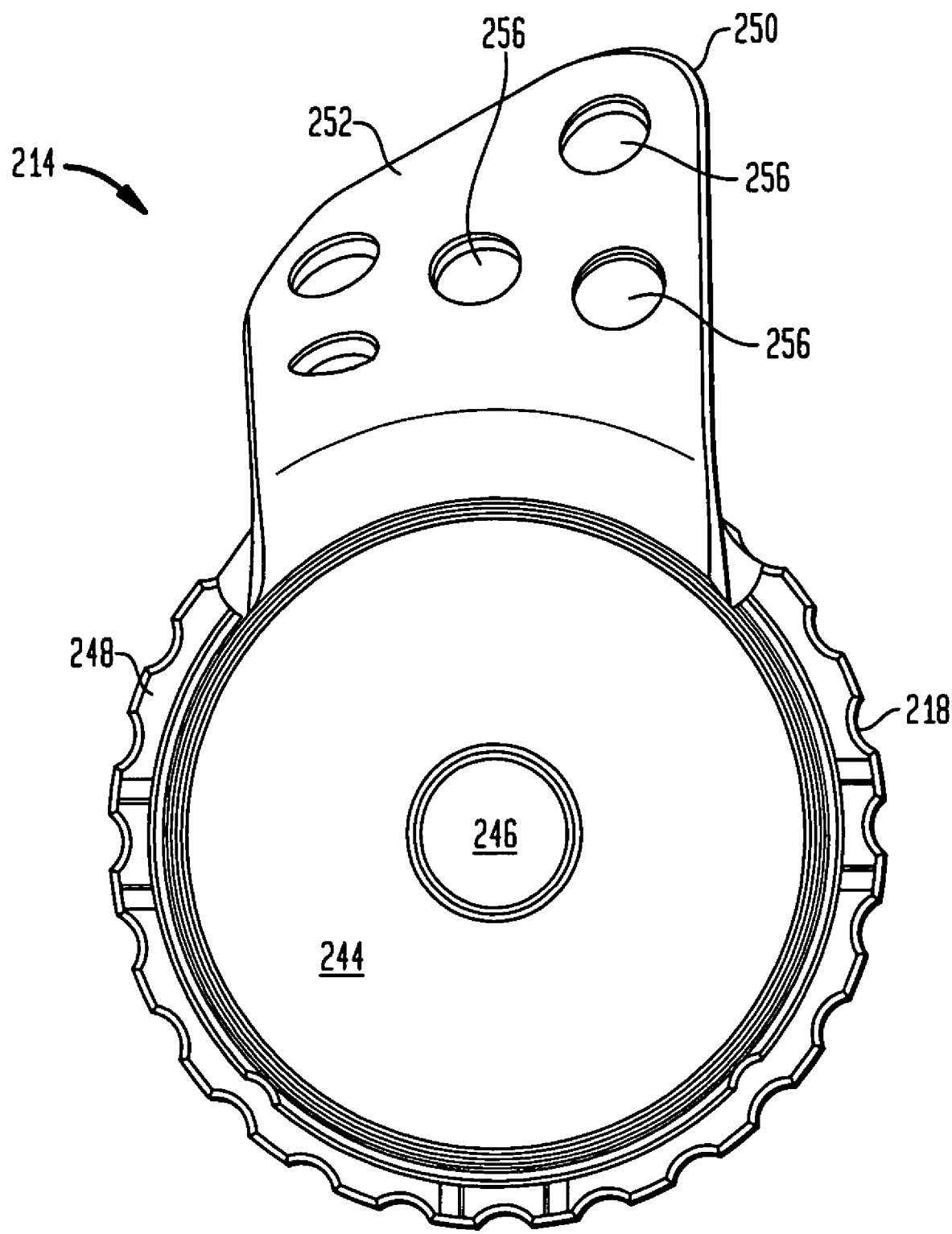
FIG. 13 is a top view of the adaptor portion of FIG. 12.
Figure 14:
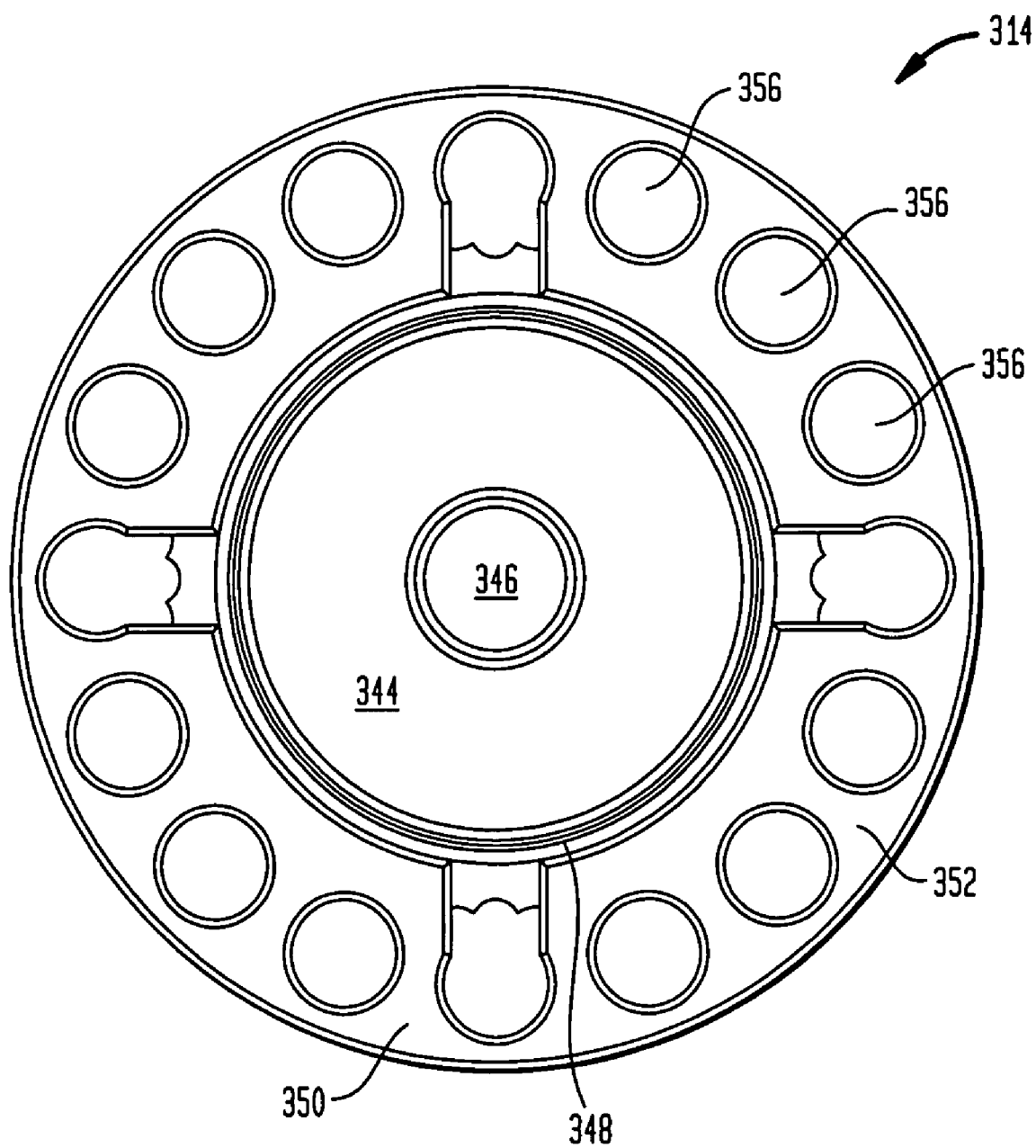
FIG. 14 is a top view of an adaptor portion of an acetabular cup replacement assembly according to another embodiment of the present invention.
Figure 15:
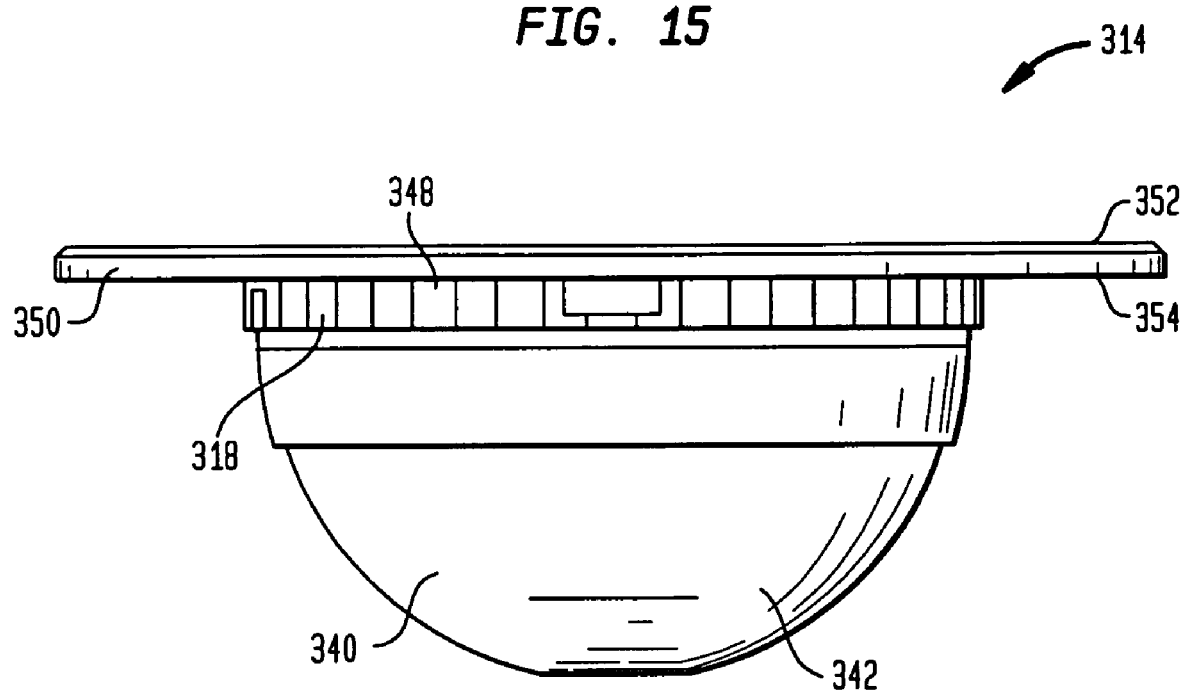
FIG. 15 is a side view of the adaptor portion of FIG. 14.
Figure 16:
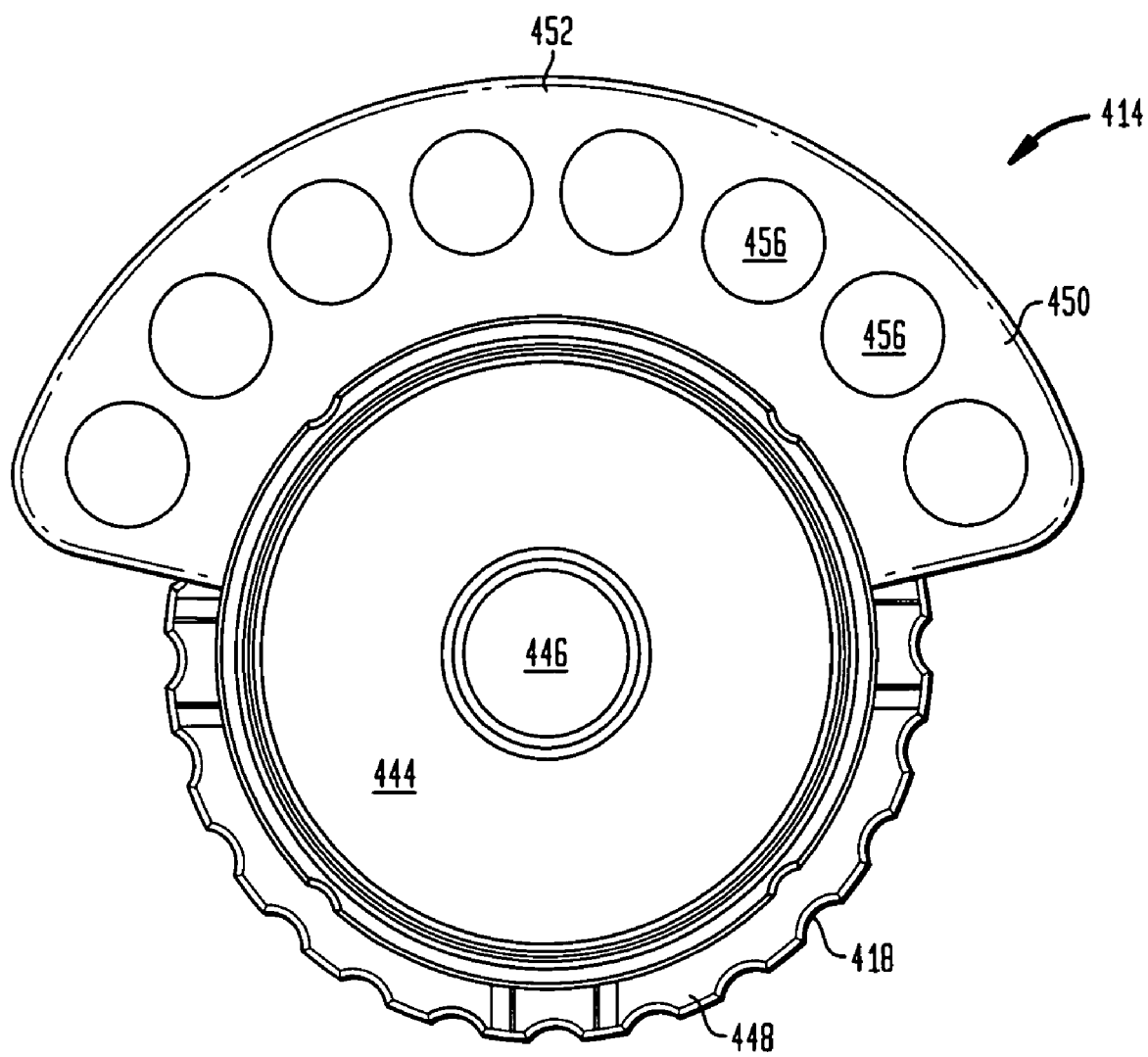
FIG. 16 is a top view of an adaptor portion of an acetabular cup replacement assembly according to another embodiment of the present invention.
Figure 17:
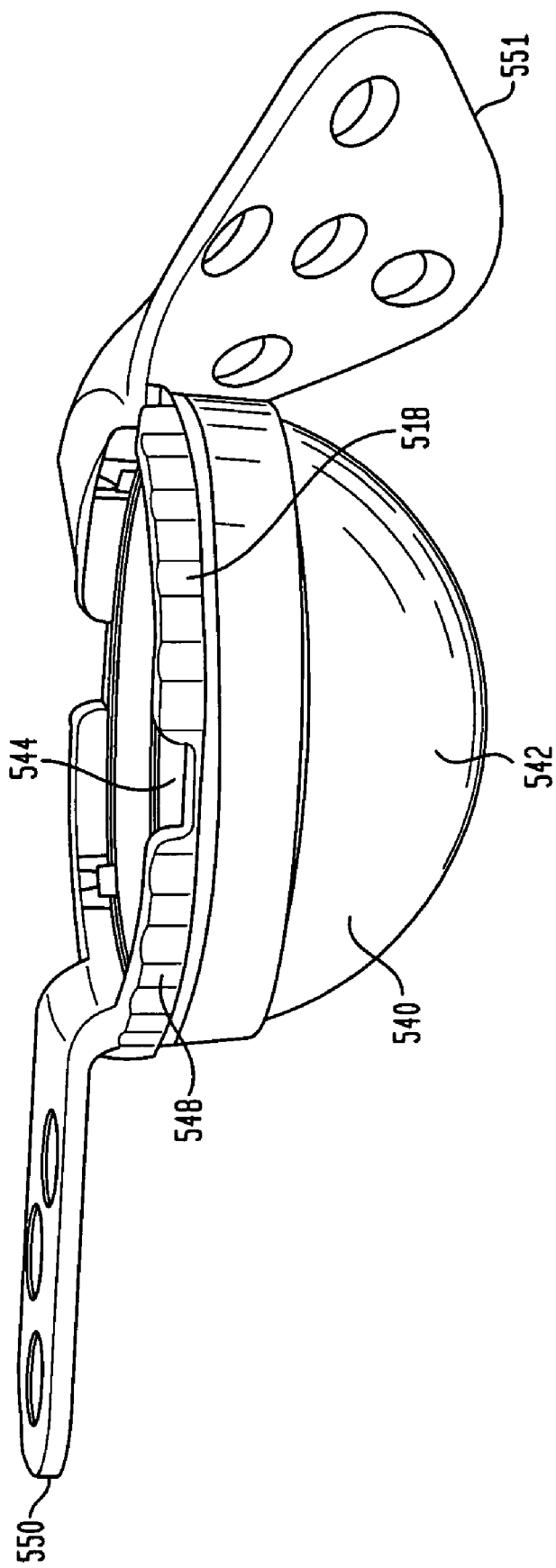
FIG. 17 is a perspective view of an adaptor portion of an acetabular cup replacement assembly according to another embodiment of the present invention.
Figure 18:
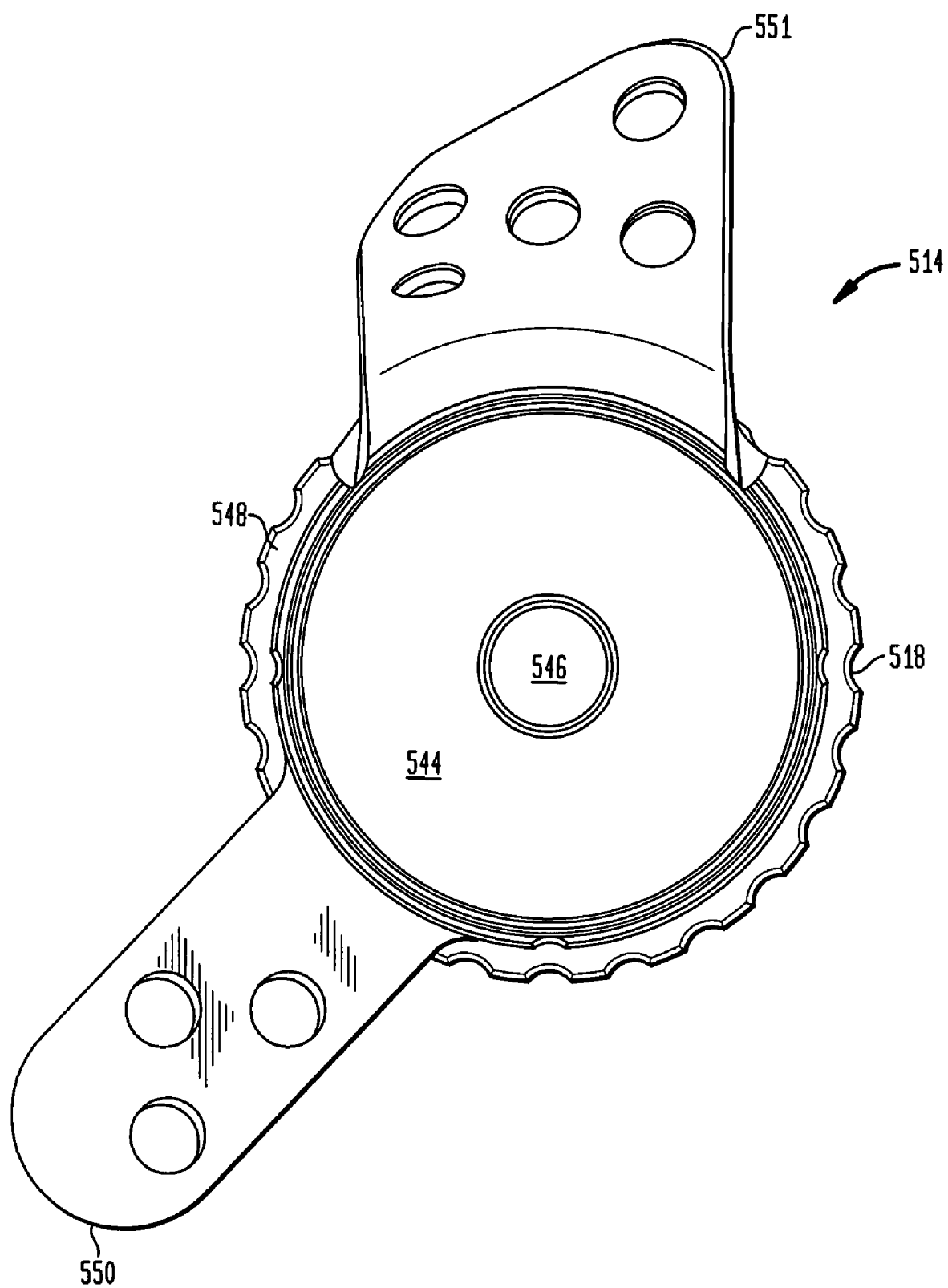
FIG. 18 is a top view of the adaptor portion of FIG. 17.

Like FIGS. 10 and 11, the remaining figures show different embodiment adaptors having similar elements, but different flanges or extensions. FIGS. 12 and 13 depict an adaptor 214 having an adaptor extension 250 similar in design to shell extension 32. FIGS. 14 and 15 depict an adaptor 314 having an adaptor extension 350 which essentially extends around the entire perimeter of rim 348. FIG. 16 depicts a similar construction adaptor 414 having an adaptor extension 450 which only extends around a portion of the perimeter of rim 448. Finally, FIGS. 17 and 18 depict an adaptor 514 which employs both an adaptor extension 550 similar in nature to adaptor extension 50, and an adaptor extension 551 similar in nature to adaptor extension 250. In this latter design, assembly 10 would ultimately include three extensions (including shell extension 32). Of course, any number of flanges or extension may be included on either the outer shell or adaptor of any given system.

It is to be understood that any of the variations discussed herein similarly apply to all embodiments disclosed herein. With regard to the alternate embodiments depicted in FIGS. 10-18, it is to be understood that any particular adaptor may be selected by a surgeon depending upon his or her preferences or the particular anatomical landscape of the patient. In this regard, it is contemplated to provide a kit in accordance with the present invention. A kit of this type would preferably allow a surgeon to make a decision as to the particular components to be utilized either before or during a surgical procedure. Among other elements, the kit would preferably include at least one outer shell 12, at least one bearing insert 16, and any number of the above-discussed adaptors 14, 114, 214, 314, 414, and 514. In addition, the kit may include various sizes of each component and could include different shells 12 and inserts 16, in accordance with the variations discussed herein or in the above-incorporated patents and patent applications. For instance, a kit in accordance with the present invention may include a series of increasing size shells 12, multiple different types of inserts 16 in similar varying sizes, and varying size adaptors with different extensions, like in adaptors 14, 114, 214, 314, 414, and 514. The kit may include one or more tools, fasteners or the like, and may be tailored to the particular patient, based upon preoperative research into the patient's anatomy and needs.

In a typical surgical operation involving the replacement of an acetabular portion of a patient, the surgeon would first take the necessary steps to prepare the acetabulum. As is mentioned above, this may be done in accordance with any well-known or hereafter developed process, and may include the removal of a certain amount of bone or other body tissue. Once the acetabulum has been prepared, the surgeon would then insert outer shell 12 through an incision in the patient and into the prepared acetabulum. Exterior surface 24 of shell 12 would ultimately abut the prepared acetabular surface, and one or more fixation elements may be inserted through apertures 28 and into the acetabular bone. In addition, shell extension 32 would be contacted with a bone surface in the general area of the acetabulum. Once in the correct position, one or more fixation elements may be inserted through apertures 38 and into this bone. All of this may be accomplished through one or more incisions and with or without the use of navigational components.

With outer shell 12 in position, the surgeon would then select an adaptor from a group of adaptors including without limitation adaptors 14, 114, 214, 314, 414, and 514. It is noted that the particular adaptor selected should be sized and shaped to properly engage shell 12, and should include a flange or extension suitable for engagement with a nearby bone. For explanation purposes, we will assume the surgeon selects adaptor 14. Adaptor 14 should then be inserted through the aforementioned incision or one of the aforementioned incisions, and into shell 12. Depending upon the desired orientation of the adaptor extension, the surgeon may need to turn adaptor 14 within shell 12 in order to achieve the correct orientation of the extension. Exterior surface 42 of adaptor 14 preferably engages at least a portion of interior surface 26 of shell 12, and a fixation element may be inserted through apertures 46 and 29. This preferably aids in the mechanical interconnection between shell 12 and adaptor 14. In addition, adaptor extension 50 would be contacted with a bone surface in the general area of the acetabulum. It is noted that this bone may vary depending upon the particular flange or extension employed by the selected adaptor. Once in the correct position, one or more fixation elements may be inserted through apertures 56 and this bone.

Finally, the surgeon would select a suitable insert 16 and similarly insert such into interior surface 44 of adapter 14. Once again, this may involve engaging insert 16 with adapter 14, depending upon the particular interconnection utilized. It is to be understood that some of the above-noted variations in relation to the particular components of assembly 10 may vary the particular method steps required in a surgical procedure. In addition, although not discussed with particularity herein, the other steps involved with a standard hip replacement procedure or the like are to be performed in accordance with the surgeon's mode of operation. Those of ordinary skill in the art would readily recognize what these steps may entail. The fact that each of outer shell 12 and adaptor 14 includes at least one flange or extension, as opposed to one or the other including all flanges or extensions, allows for the easier manipulation and implantation of assembly 10. In previous assemblies, one of an outer shell or an adaptor would include multiple opposed flanges or extensions. This would make it difficult to position the flanges or extensions around soft tissue and directly against bone. In accordance with the present invention, the inclusion of one flange or extension on each of outer shell 12 and adaptor 14 allows a surgeon to more easily achieve this positioning, with minimal repositioning or ancillary movement of soft tissue or the like. Thus, the present invention provides for an easier positioned and implanted assembly 10.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An acetabular cup assembly for a prosthetic hip joint comprising:
    an outer shell for attachment to the acetabulum, the outer shell having an inner surface, an outer periphery, and at least one radially extending shell extension with first and second shell extension apertures, the shell extension apertures designed to receive first fasteners for fixing the outer shell to bone;
    a bearing insert; and
    an adaptor having an outer surface for engaging the inner surface of the outer shell, an inner surface for receiving the bearing insert, and at least one radially extending adaptor extension with first and second adaptor extension apertures, the adaptor extension apertures extending beyond the outer periphery of the outer shell and designed to receive second fasteners for fixing the adaptor to bone, wherein the first adaptor extension aperture extends radially further than the second adaptor extension aperture.

2. The acetabular cup assembly as set forth in claim 1, wherein the at least one shell extension further includes a third shell extension aperture and the at least one adaptor extension further includes a third adaptor extension.

3. The acetabular cup assembly as set forth in claim 1, wherein at least one of the at least one shell extension and at least one adaptor extension are deformable at least in one direction.

4. The acetabular cup assembly as set forth in claim 3, wherein at least one of the at least one shell extension and at least one adaptor extension include a reduced cross-section to facilitate the deformation.

5. The acetabular cup assembly as set forth in claim 4, wherein the reduced cross-section is formed by a groove.

6. The acetabular cup assembly as set forth in claim 3, wherein both the at least one shell extension and the at least one adaptor extension are deformable.

7. The acetabular cup assembly as set forth in claim 1, wherein the inner surface of the outer shell and the outer surface of the adaptor have complimentary tapered locking surfaces.

8. The acetabular cup assembly as set forth in claim 7, wherein the adaptor includes a plurality of anti-rotation scallops for cooperation with complimentary structure on the outer shell.

9. The acetabular cup assembly as set forth in claim 1, wherein the at least one shell extension is shaped to cooperate with an illium.

10. The acetabular cup assembly as set forth in claim 1, wherein the at least one adaptor extension is shaped to cooperate with an ischium.

11. The acetabular cup assembly as set forth in claim 1, wherein the adaptor includes a rim area, the at least one adaptor extension extending from the rim area.

12. A kit for resurfacing an acetabulum comprising:
    at least one outer shell for attachment to the acetabulum, the outer shell having an inner surface, an outer periphery, and at least one radially extending shell extension with first and second shell extension apertures, the shell extension apertures designed to receive first fasteners for fixing the outer shell to bone;
    at least one bearing insert; and
    a plurality of adaptors each having an outer surface for engaging at least a portion of the inner surface of the outer shell, an inner surface for receiving the bearing insert and at least one radially extending adaptor extension with first and second adaptor extension apertures, the adaptor extension apertures extending beyond the outer periphery of the outer shell and designed to receive second fasteners for fixing the adaptor to bone, wherein the first adaptor extension aperture extends radially further than the second adaptor extension aperture.

13. The kit according to claim 12, wherein the inner surface of the outer shell and the outer surfaces of the plurality of adaptors have complimentary tapered locking surfaces.

14. The kit according to claim 13, wherein the plurality of adaptors each include a plurality of anti-rotation scallops for cooperation with a complimentary structure on the outer shell.

15. The kit according to claim 12, wherein the inner surfaces of the plurality of adaptors and an outer surface of the at least one bearing insert have complimentary locking surfaces.

16. The kit according to claim 12, wherein the at least one adaptor extension varies for each adaptor.

* * * * *

UNITED STATES PATENT AND TRADEMARK OFFICE
CERTIFICATE OF CORRECTION

PATENT NO.        : 7,682,399 B2                                        Page 1 of 1
APPLICATION NO.   : 11/810829
DATED             : March 23, 2010
INVENTOR(S)       : William Hale Shields and Viktor Erik Krebs It is certified that error appears in the above-identified patent and that said Letters Patent is hereby corrected as shown below:

Column 8, line 27, "adaptor extension." should read --adaptor extension aperture.--.

Signed and Sealed this
Eighth Day of March, 2011

David J. Kappos
*Director of the United States Patent and Trademark Office*